(12) United States Patent
Kiraly et al.

(10) Patent No.: US 10,390,726 B2
(45) Date of Patent: Aug. 27, 2019

(54) SYSTEM AND METHOD FOR NEXT-GENERATION MRI SPINE EVALUATION

(71) Applicant: Siemens Healthcare GmbH, Erlangen (DE)

(72) Inventors: Atilla Peter Kiraly, Plainsboro, NJ (US); David Liu, Richardson, TX (US); Shaohua Kevin Zhou, Plainsboro, NJ (US); Dorin Comaniciu, Princeton Junction, NJ (US); Gunnar Krüger, Watertown-Boston, MA (US)

(73) Assignee: Siemens Healthcare GmbH, Erlangen (DE)

( * ) Notice: Subject to any disclaimer, the term of this patent is extended or adjusted under 35 U.S.C. 154(b) by 372 days.

(21) Appl. No.: 15/471,250

(22) Filed: Mar. 28, 2017

(65) Prior Publication Data
US 2017/0273593 A1    Sep. 28, 2017

Related U.S. Application Data

(60) Provisional application No. 62/313,863, filed on Mar. 28, 2016.

(51) Int. Cl.
*A61B 5/055* (2006.01)
*A61B 5/00* (2006.01)
*G06T 19/20* (2011.01)

(52) U.S. Cl.
CPC .............. *A61B 5/055* (2013.01); *A61B 5/407* (2013.01); *A61B 5/4566* (2013.01); *A61B 5/7264* (2013.01); *G06T 19/20* (2013.01); *A61B 2576/02* (2013.01)

(58) Field of Classification Search
CPC ..... A61B 2576/02; A61B 5/055; A61B 5/407; A61B 5/4566; A61B 5/7264; G06T 7/0012
See application file for complete search history.

(56) References Cited

U.S. PATENT DOCUMENTS

| 8,423,124 B2 * | 4/2013 | Kiraly | ................... A61B 5/103 |
| | | | 600/425 |
| 2013/0070996 A1 * | 3/2013 | Liu | ......................... G06K 9/00 |
| | | | 382/131 |

OTHER PUBLICATIONS

Michael Kelm, B., Wels, M., Kevin Zhou, S., Seifert, S., Suehling, M., Zheng, Y., & Comaniciu, D. (2013). Spine detection in CT and MR using iterated marginal space learning. Medical Image Analysis, 17(8), 1283-1292. http://doi.org/10.1016/j.media.2012.09.007.

* cited by examiner

*Primary Examiner* — Michael T Rozanski

(57) ABSTRACT

A method of visualizing spinal nerves includes receiving a 3D image volume depicting a spinal cord and a plurality of spinal nerves. For each spinal nerve, a 2D spinal nerve image is generated by defining a surface within the 3D volume comprising the spinal nerve. The surface is curved such that it passes through the spinal cord while encompassing the spinal nerve. Then, the 2D spinal nerve images are generated based on voxels on the surface included in the 3D volume. A visualization of the 2D spinal images is presented in a graphical user interface that allows each 2D spinal image to be viewed simultaneously.

7 Claims, 10 Drawing Sheets

_US 10,390,726 B2_

SYSTEM AND METHOD FOR NEXT-GENERATION MRI SPINE EVALUATION

CROSS-REFERENCE TO RELATED APPLICATIONS

This application claims the benefit of U.S. Provisional Application Ser. No. 62/313,863 filed Mar. 28, 2016, which is incorporated herein by reference in its entirety.

TECHNICAL FIELD

The present disclosure relates generally to methods, systems, and apparatuses for evaluating Magnetic Resonance Imaging (MRI) images of the spine using automation of scanning, reformation, and examination processes employed during examination.

BACKGROUND

Magnetic Resonance Imaging (MRI) images of the spine provide superior diagnostic capabilities for examination of a variety of abnormalities and trauma injuries. A scout scan is first performed followed by sagittal T1, and sagittal and transverse T2 imaging. Diffusion weighted imaging (DWI), Short tau inversion recovery (STIR), and contrast imaging may also be performed depending upon the patient. Findings include stenosis, neural foramina stenosis, disc pathology, ligaments defects, fractures, and findings in the marrow. Each radiologist has certain reading patterns for examining the image based on personal preference and case history. Clinical Decision Systems (CDS) assist in standardized reporting and further treatment recommendations by filling out a report structure and references based upon any findings. Although CDS can assist in filling out a final report, the task of detecting and detailing findings still falls upon the radiologist. Assistance and automation in this process can lead to faster readings with reduced errors.

Currently, readings commonly occur at picture archiving and communications systems (PACS). In some cases, images can be manually reformatted by a technician to make reading easier. CDS systems can help in automation of the report generated but do little in helping analyze the image itself. Previously, Computer Aided Detection (CAD) systems have been proposed, but they are lacking for two major reasons. First, CAD systems are focused on one particular type of abnormality and do not benefit all aspects of reading. Secondly, radiologists have a preferred reading order that can result in increased errors or reading time if disturbed. CAD and CDS Systems can disturb this reading order.

SUMMARY

Embodiments of the present invention address and overcome one or more of the above shortcomings and drawbacks, by providing methods, systems, and apparatuses for evaluating Magnetic Resonance Imaging (MRI) images of the spine using automation of scanning, reformation, and examination processes employed during examination.

According to some embodiments, a method of visualizing spinal nerves includes receiving a 3D image volume depicting a spinal cord and spinal nerves. For each spinal nerve, a 2D spinal nerve image is generated by defining a surface within the 3D volume comprising the spinal nerve. The surface is curved such that it passes through the spinal cord while encompassing the spinal nerve. Then, the 2D spinal nerve images are generated based on voxels on the surface included in the 3D volume. A visualization of the 2D spinal images is presented in a graphical user interface that allows each 2D spinal image to be viewed simultaneously.

Various additional features, enhancements, and other modifications may be made to the aforementioned method in different embodiments. For example, in some embodiments, the visualization presents the 2D spinal images stacked according to their location along the spine. The aforementioned method may include identifying a spinal cord landmark and spinal nerve landmarks within the 3D image volume. Then, the surface may be defined within the 3D volume as a curved surface comprising the spinal cord landmark and the spinal nerve landmark. In some embodiments, the orientation of the 3D image volume is determined using a scout scan of the spinal cord and the spinal nerves. In other embodiments, a spinal cord centerline and a location on the transverse process are determined based on the 3D volume. The surface may then be defined by rotating the location on the transverse process by a pivot to arrive at an approximate location associated with the spinal nerve. This pivot may be defined, for example, based on a vertebral body included in the 3D image volume.

In some embodiments of the aforementioned method clinical findings are input by a user via the graphical user interface. These clinical findings may then be used as input into a clinical decision support reasoning engine to determine one or more treatment recommendations. In one embodiment, a deep learning network is used to locate one or more degenerative spinal elements (e.g., discs, spine, bone marrow) in the 3D image volume. The deep learning network may include, for example, 3 convolutional layers and 3 fully connected layers trained to label volumetric regions as containing normal or degenerative spinal elements. Once the degenerative spinal elements are determined, they may be also input into the clinical decision support reasoning engine to determine the one or more treatment recommendations.

According to another aspect of the present invention, a computer-implemented method for generating inputs for clinical decision support engine based on unfolded spinal image data includes receiving a 3D image volume depicting a spinal cord, vertebra, and spinal nerves. The spinal nerves depicted in the 3D image volume are unfolded to yield unfolded spinal nerves. Unfolded spinal nerve images are generated which depict the unfolded spinal nerves. Similarly, the vertebra depicted in the 3D image volume is unfolded and used to generate unfolded vertebra images depicting the unfolded vertebra. Then, degenerative spinal elements may be determined based on the unfolded spinal nerve images and the unfolded vertebra images. For example, in one embodiment, the degenerative spinal elements are determined based on input received from a clinician in response to presentation of the unfolded spinal nerve images and the unfolded vertebra images on a display. In other embodiments, the degenerative spinal elements are determined automatically by a machine learning network using the spinal nerve images and the unfolded vertebra images as input. Once determined, the degenerative spinal elements may be documented in a clinical decision support reasoning engine or a similar form of automated reporting.

In other embodiments of the present invention, a computer-implemented method of viewing spinal imaging data includes identifying landmarks in the 3D image volume. The landmarks comprise a spinal cord landmark, and one or more vertebral body landmarks. Left and right sagittal slices are selected from the 3D image volume. The left sagittal slice comprises the vertebral body landmarks on a left lateral side of the spinal cord landmark, while the right sagittal slice comprises the vertebral body landmarks on a right lateral side of the spinal cord landmark. A visualization is presented in a graphical user interface that displays the left sagittal slice and the right sagittal slice side-by-side. In some embodiments, a request is received via the GUI to move the left sagittal slice and the right sagittal slice in a distal or proximal direction with respect to the spinal cord landmark. In response to receiving this request, selecting a new left and right sagittal slice are selected and presented side-by-side as a new visualization in the graphical user interface.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures.

DETAILED DESCRIPTION

The following disclosure describes the present invention according to several embodiments directed at methods, systems, and apparatuses related to evaluating Magnetic Resonance Imaging (MRI) images of the spine using automation of scanning, reformation, and examination processes employed during examination. Current diagnosis and reporting methods can be improved in terms of accuracy and speed by systematically addressing bottlenecks and weaknesses in workflow. However, any changes should not greatly disrupt the radiologists' current workflow as it has been shown to reduce their accuracy. The techniques described herein employ complete series of methods to address these issues to assist CDS tools and workflows without interfering with the current workflow.

Figure 1A:
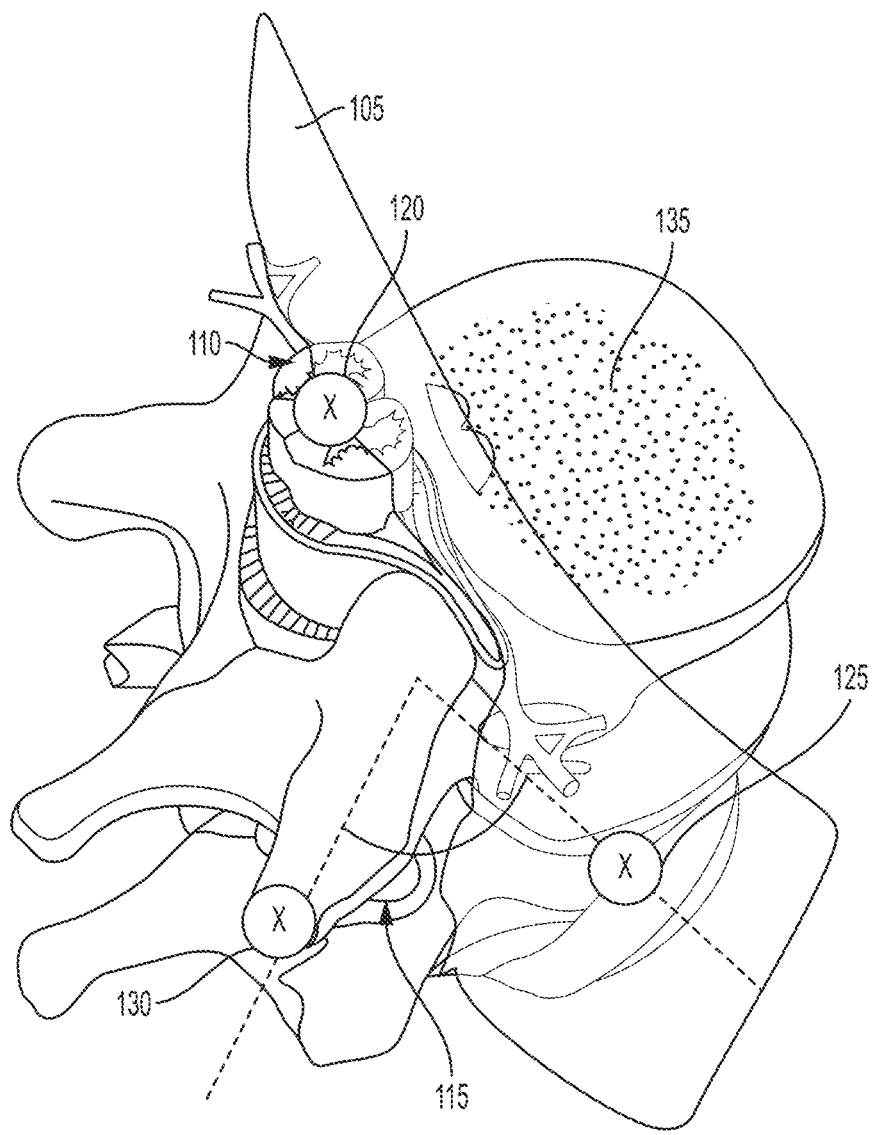
FIG. 1A illustrates the proposed technique for nerve unfolding for neural foramina stenosis, according to some embodiments.

Briefly, the methods described herein comprise three features: scanning automation, reformation automation, and examination automation. Scanning automation is provided by assisting clinicians and technicians in determining orientation of subsequent scans based on scout scan. Additional scanning automation techniques generally known in the art may also be incorporated into the techniques described herein. Reformation automation is provided in four respects. First, starting with spine parsing of the volumetric T1 or T2 image for structure (see FIG. 3A), the centerline and nerve regions can be identified. Secondly, bone-based reformation techniques may be automatically delivered to the PACS. Third, nerve-based reformation may be applied to allow for easy identification of neural foramina stenosis (see FIGS. 1A, 1B, and 2). Fourth, reformations may be applied that allow for easy comparison of different time points.

The examination automation techniques described herein include six features. First, abnormalities are automatically detected using deep learning methods. Secondly, the portion of the examination the radiologist is currently performing is determined, for example, based on previous preferences set by radiologist, application inputs such as window/level and slice, and/or eye-tracking methods to determine which region is under examination. Third, the findings presented to the radiologist may be limited to current task at hand or findings that relevant to the current findings being input by the radiologist. Fourth, regions with large appearance changes in different time points may be highlighted. Fourth, a patch view display (see, e.g., FIGS. 3B and 3C) may be used for simultaneous region viewing.

FIG. 1 illustrates the proposed technique for nerve unfolding for neural foramina stenosis, according to some embodiments. The term "unfolding," as used herein refers to flattening of a curved object in a 3D image volume into a two dimensional image. A multi-planar reconstruction of the volumetric image data is presented to the physician. The illustration shows the curved surface 105 about which the reconstruction occurs to include the spinal cord 110 and neural foramina 115 (i.e. the openings in the vertebrae that allow the nerve roots to connect to the rest of the body). As the curved surface 105 can be adjusted in the anterior-posterior directions, the bone can be analyzed in addition to peripheral spinal nerves. Compared to existing 2D transverse and coronal imaging plane, reconstruction of the spine image with the movable curved surface 105 allows for more nerves regions to be analyzed without scrolling. The curvature of the plane of the curved surface 105 is "gentle" in that little distortion will occur over the nerve to allow for a straightforward interpretation of nerve stenosis.

The definition of this curved surface 105 shown in FIG. 1 can be done, for example, by landmark detection of the spinal cord and the distal nerves (shown by markers 120, 125, and 130) using techniques generally known in the art. Example techniques for landmark detection are described in Michael Kelm, B., Wels, M., Kevin Zhou, S., Seifert, S., Suehling, M., Zheng, Y., & Comaniciu, D. (2013). Spine detection in CT and MR using iterated marginal space learning. Medical Image Analysis, 17(8), 1283-1292, the entirety of which is incorporated herein by reference. Once the landmarks are detected, the curved surface may be defined as a surface including all of the landmarks.

Figure 1B:
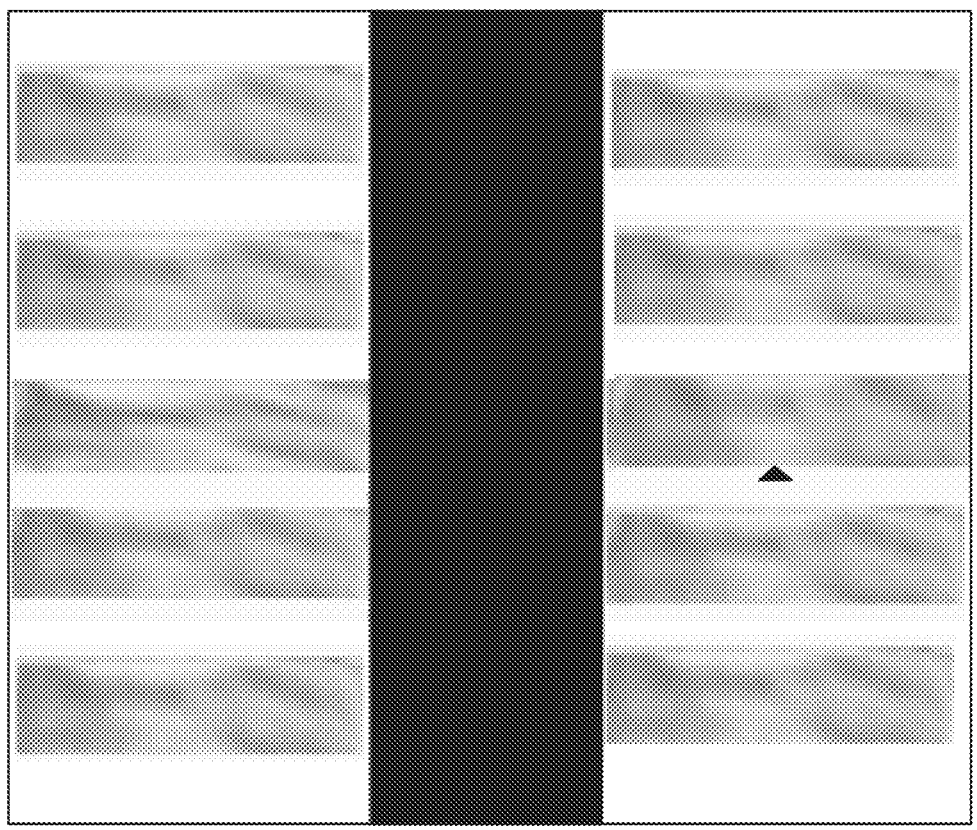
FIG. 1B shows an example of the unfolded view of spinal nerves.

Alternatively, the spinal cord centerline can be located along with the transverse process (shown by markers 120 and 130). In general any technique known in the art may be used for locating the spinal cord centerline and transverse process. For example, in some embodiments, the centerline is determined using a fully automatic spinal cord tracing-based method as described in U.S. Pat. No. 8,423,124 to Kiraly et al., issued Apr. 16, 2013, entitled "Method and system for spine visualization in 3D medical images," the entirety of which is incorporated herein by reference. Once the centerline is determined, the plane can then be defined by rotating location by a pivot to arrive at the approximate nerve location (as shown by the dotted lines in FIG. 1). The angle and pivot of rotation can vary based on the vertebral body 135. FIG. 1B shows an example of the unfolded view. In cases where the resolution of the data is anisotropic or limited, the unfolded reconstructions can have artifacts present.

Figure 1C:
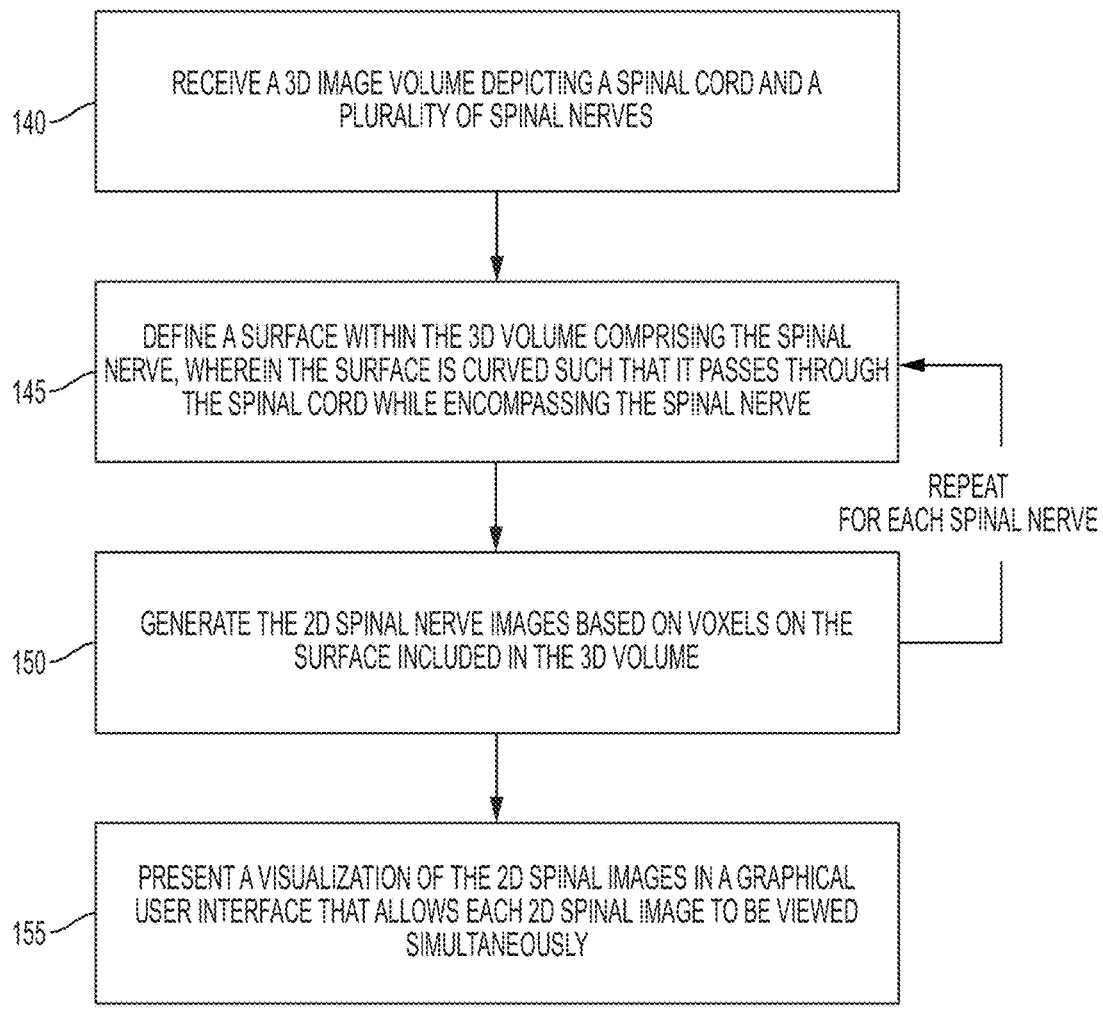
FIG. 1C illustrates a method for visualizing spinal image data using the technique described above with reference to FIG. 1A, according to some embodiments.

FIG. 1C illustrates a method for visualizing spinal image data using the technique described above with reference to FIG. 1A, according to some embodiments. Starting at step 140, a 3D image volume is received by a computing system. "Receiving" may entail, for example, acquiring the image volume directly or loading a previously generated volume from a storage medium. The 3D image volume, as is generally understood in the art, comprises a plurality of voxels in a 3D structure. The volume depicts the spinal region of a patient, including the patient's spinal cord and a plurality of spinal nerves.

Next, at steps 145 and 150, a 2D image is generated for each spinal nerve. These images are referred to herein as a "2D spinal nerve images." At step 145, a surface is defined within the 3D volume as described above with reference to FIG. 1A. This surface includes the spinal nerve being analyzed and the surface is curved such that it passes through the spinal cord while encompassing the spinal nerve. The two example methods described above for generating the surface may be applied at step 145. Thus, in some embodiments, landmarks are detected on the spinal cord (a "spinal cord landmark") as well as on the spinal nerves ("spinal never landmarks"). The surface may then be defined within the 3D volume as a curved surface comprising the spinal cord landmark and the spinal nerve landmark. These landmarks may be specified by a clinician via a graphical user interface or, alternatively, automatic landmark detection techniques generally known in the art may be applied. As an alternative to the landmark detection-based method, in other embodiments, the spinal cord centerline is identified along with a location on a transverse process within the 3D volume. Again, manual or automatic methods may be applied in identifying the centerline and the transverse process. The surface may then be defined by rotating the location on the transverse process by a pivot such as a vertebral body to arrive at an approximate location associated with the spinal nerve. Following step 150, the process repeats for the other spinal nerves. In some embodiments, rather than sequentially processing each nerve, a parallel processing computing platform is used to process multiple nerves in parallel.

Continuing with reference to FIG. 1C, at step 155, a visualization of the 2D spinal images in a graphical user interface (GUI) that allows each 2D spinal image to be viewed simultaneously. The visualization shown in FIG. 1B is one example of a visualization that may be presented at step 155; however, it should be understood that other visualizations can be used in other embodiments. A clinician can then determine clinical findings based on this visualization. These findings may include, for example, an identification of degenerative spinal elements (e.g., discs, spine, bone marrow, etc.). As described in further detail below with reference to FIG. 4, the clinical findings can then be input via the GUI to a clinical decision support reasoning engine to determine one or more treatment recommendations. In some embodiments, rather than requiring the clinician to manually enter the clinical findings, a deep learning model may be used to generate the findings automatically based on the spinal nerve images.

Figure 2:
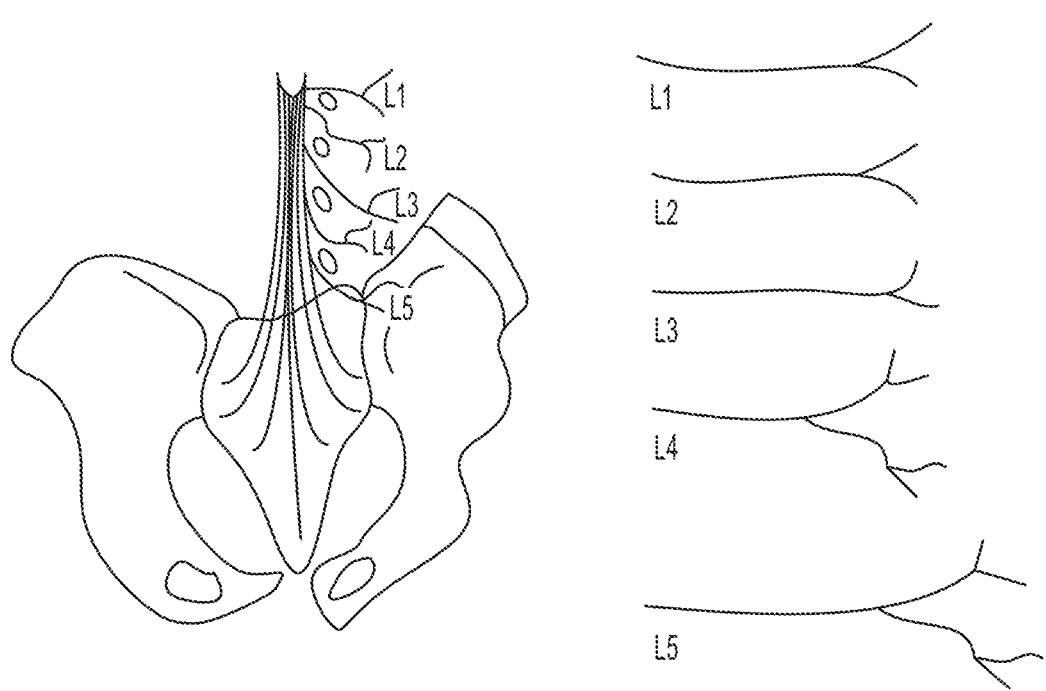
FIG. 2 illustrates an example visualization where spinal nerves are segmented and unfolded into a single 2D view.

As an alternative to the techniques described above with reference to FIGS. 1A-1C, in other embodiments, a slice stacking method may be used for visualization as shown schematically in FIG. 2. When given a volume of sufficient quality, the centerlines of the nerves are segmented and identified. Then, the nerves can be unfolded or unraveled into a single 2D view. FIG. 2 shows the nerve structure of the entire captured volume. The segmentation and centerlines can then be used to detect abnormalities such as stenosis. Additionally, the volume regions about the centerline (i.e., voxels on each side of the centerline) can be selected and used to visualize the image data about the nerves. On the right-hand side of FIG. 2, the corresponding nerves are individual isolated and flattened with bifurcations preserved to allow for a single uncluttered view of all of the nerves.

Unfolding of spinal bones may be performed by adopting techniques previously applied to rib unfolding techniques. Examples of such techniques are described in U.S. Patent Application Publication No. 2013/0070996, "Method and System for Up-Vector Detection for Ribs in Computed Tomography Volumes", D. Liu et al., published on Mar. 21, 2013 and U.S. Pat. No. 7,627,159, "2D Visualization for Rib Analysis", A. Kiraly et al., issued on Dec. 1, 2009, each of which is hereby incorporated by reference for all purposes. These techniques allow for the unfolding of the 3D rib cage image into a 2D image to improve examination time and reduce ambiguity in interpreting the CT data of the ribs.

Figure 3A:
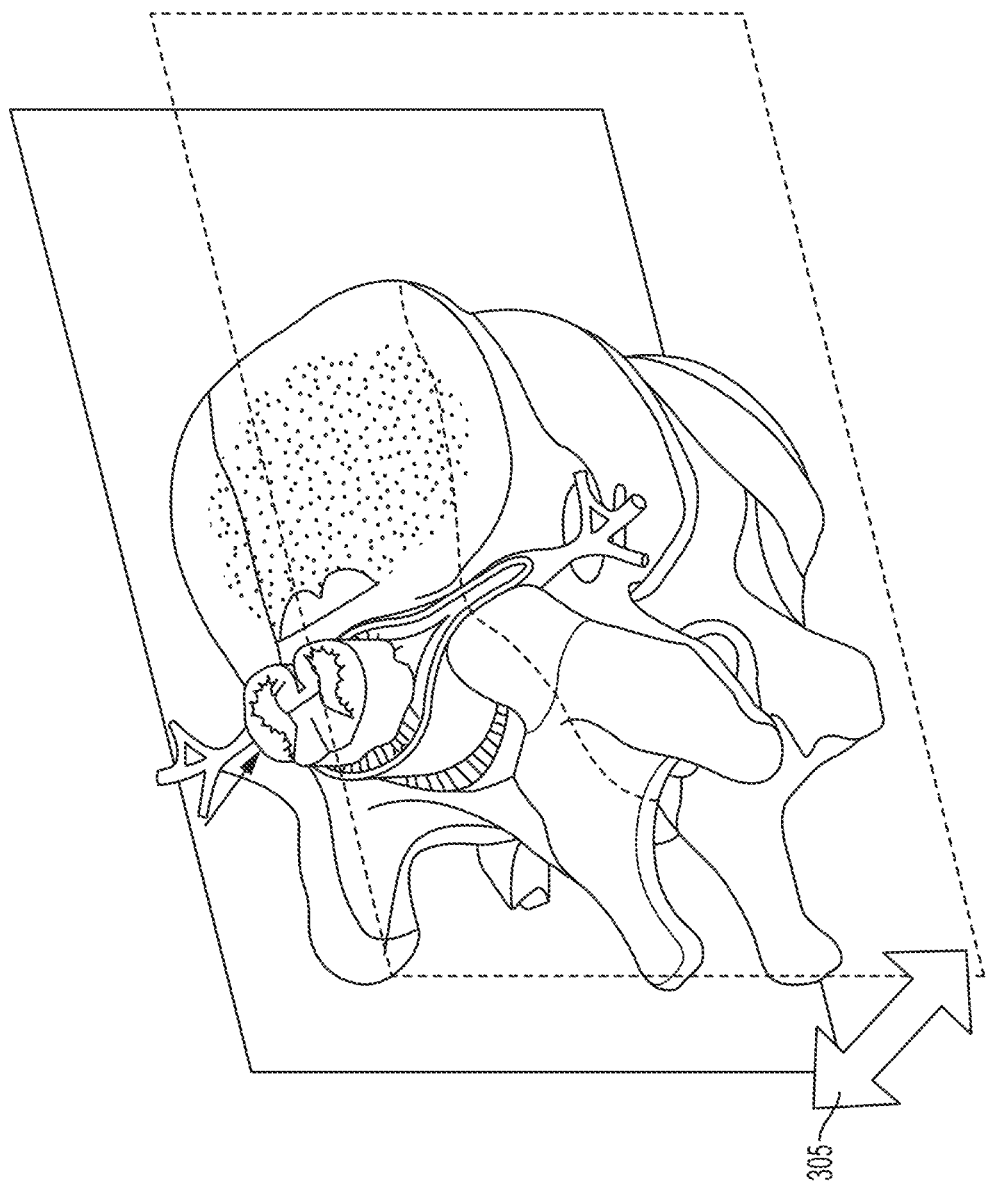
FIG. 3A shows a viewing interface for accessing the spinal cord and neural foramina regions in axial and sagittal multi-modality images, according to some embodiments.
Figure 3B:
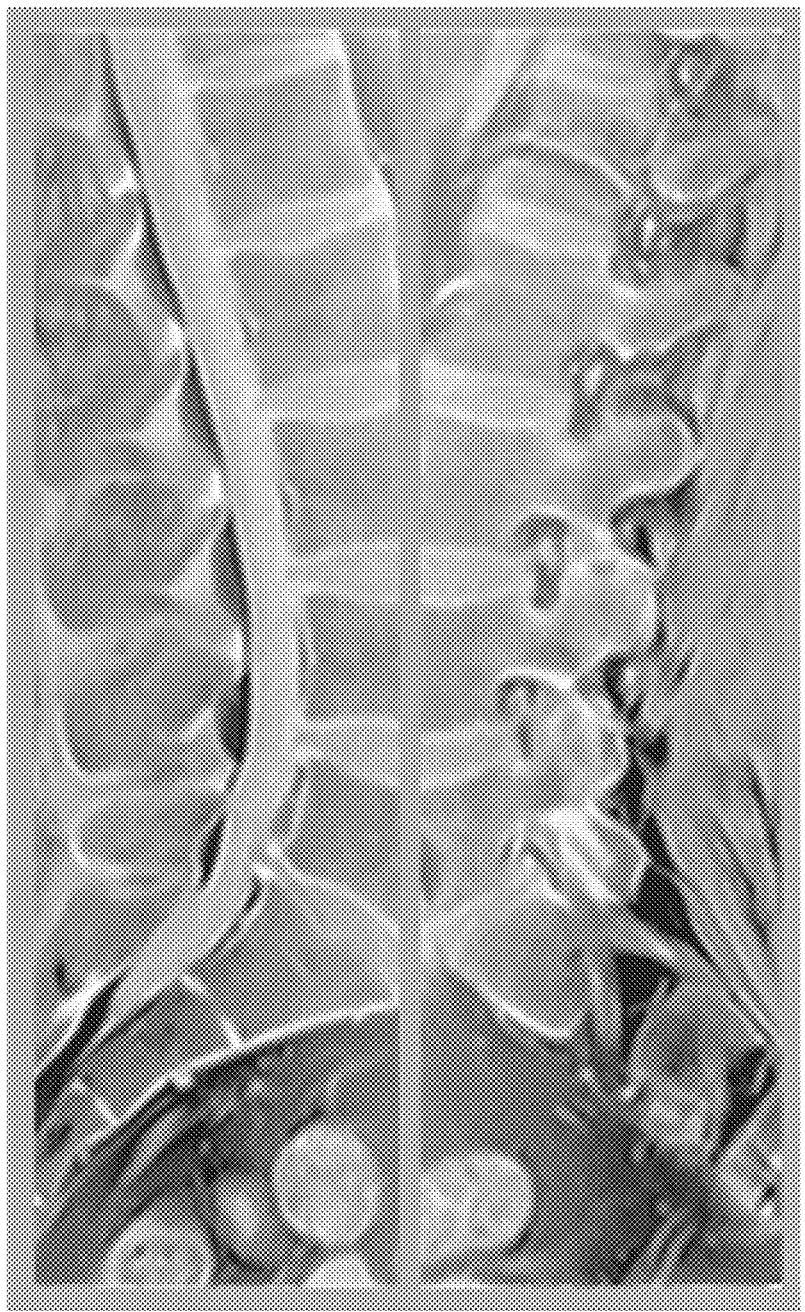
FIG. 3B shows an example visualization of sagittal image slices, according to some embodiments.
Figure 3C:
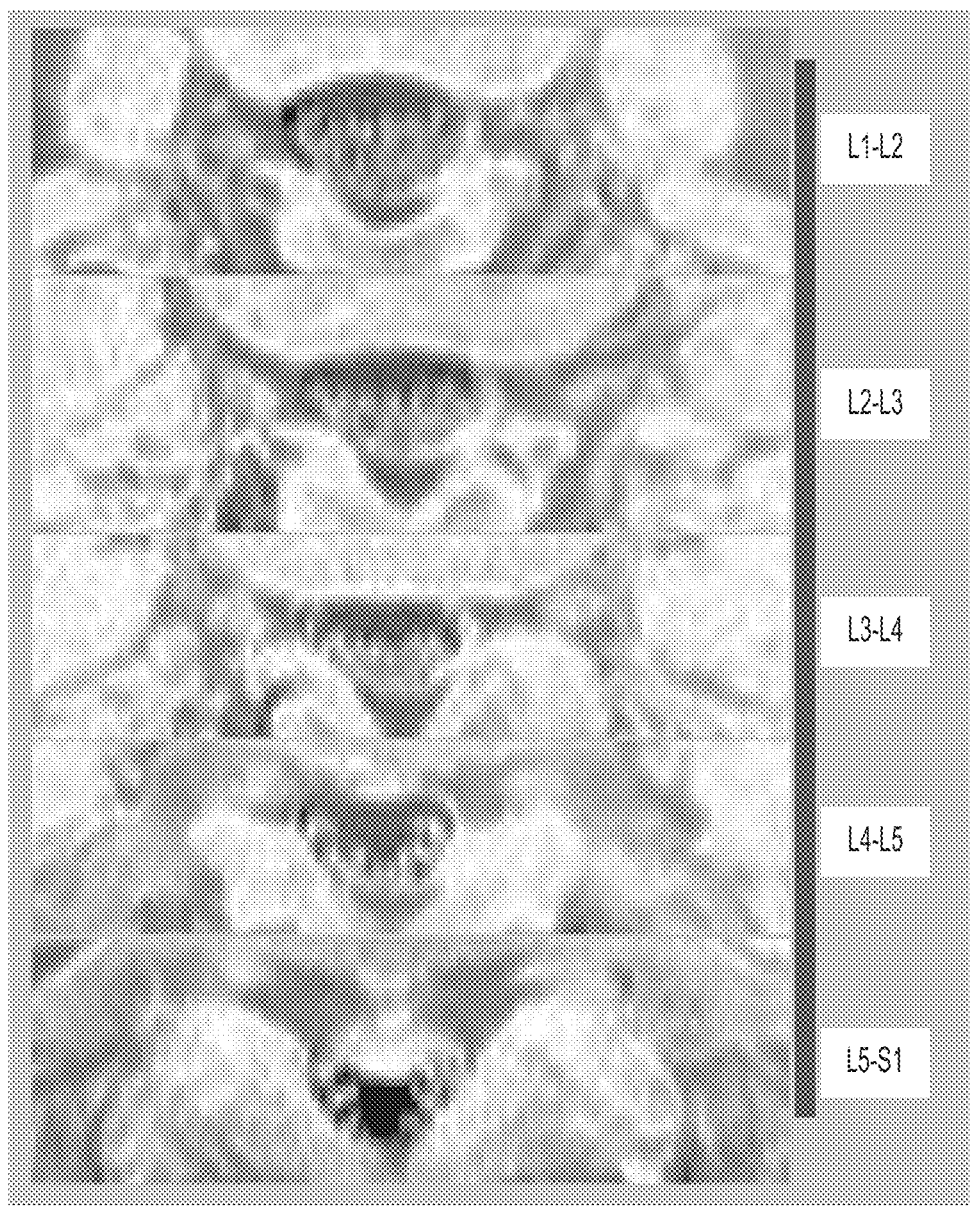
FIG. 3C shows an example visualization of transverse image slices, according to some embodiments.

FIG. 3A illustrates a viewing interface for accessing the spinal cord and neural foramina regions in axial and sagittal multi-modality images, according to some embodiments. In this example, the images are used directly without reformations by stacking portions of each image and providing a uniform control within each view. The result is that less interaction is necessary to review the spine and isotropic high-resolution images are not necessary. The sagittal slice planes are taken directly from the volume and simultaneously shown as demonstrated in FIG. 3B. As the user scrolls though the slices, they simultaneously approach or diverge from each other as shown in FIG. 3A (arrow 305). Alternatively, with transversely sliced volumes, each vertebra and spinal cord region can be shown simultaneously again with uniform controls as shown in FIG. 3C. In each case, the physician can examine to compare and contrast the left and right regions of the patient. All views can be shown or a swap operation can be performed to switch between the views. The prerequisites to achieve these views are the detection of several landmarks within the image (e.g., spinal cord and vertebral bodies). When detected, the labels can also be presented with each image patch shown.

Figure 3D:
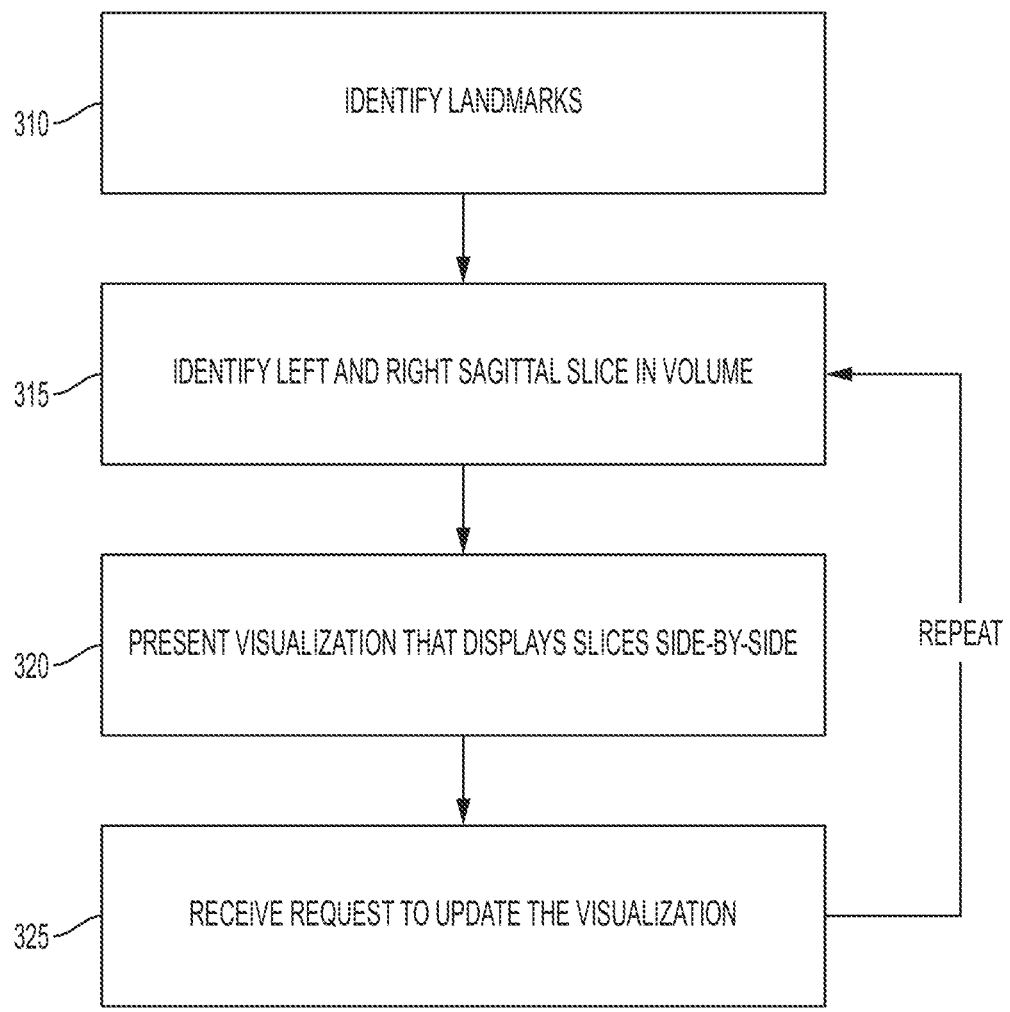
FIG. 3D provides a flowchart which summarizes the technique described above with respect to FIGS. 3A-3C, according to some embodiments.

FIG. 3D provides a flowchart which summarizes the technique described above with respect to FIGS. 3A-3C, according to some embodiments. Starting at step 310 a plurality of landmarks is identified in the 3D image volume. These landmarks may include, for example, a spinal cord landmark, and one or more vertebral body landmarks. Next, at step 315, a left sagittal slice and a right sagittal slice are identified in the image volume based on the landmarks. The left sagittal slice contains the vertebral body landmarks on a left lateral side of the spinal cord landmark, while the right sagittal slice contains the vertebral body landmarks on a right lateral side of the spinal cord landmark. Finally, at step 320 a visualization is presented in a GUI that displays the left sagittal slice and the right sagittal slice side-by-side (see FIG. 3B). Optionally, after the visualization is displayed an update request may be received via the GUI at step 325. The update request may take the form of, for example, a user scrolling through or clicking on a portion of the GUI. The request essentially indicates the user's desire to move the left sagittal slice and the right sagittal slice in a distal or proximal direction with respect to the spinal cord landmark. For a request to move in the distal direction can be specified by scrolling in one direction, while a request to move in a proximal direction may be specified by scrolling in the opposite direction. After the update request has been received, the location is updated in the image volume and new sagittal slices are selected starting at step 315.

The approaches shown in FIG. 1-FIG. 3D can be used to detect and diagnose the images in the same way as radiologists are trained but with the added advantage of having to perform less scrolling tasks and to be able to simultaneously compare left and right sides and different vertebra of the patient. In the case of a finding, all regions relate back to the original volume. Based upon the data from the landmarks, the region of the patient selected (e.g., clicked) can be automatically fed to a CDS for documentation. Furthermore, a deep learning model can be used to identify and quantify the abnormality based on the given location and any previous patient history including lab work.

Figure 4:
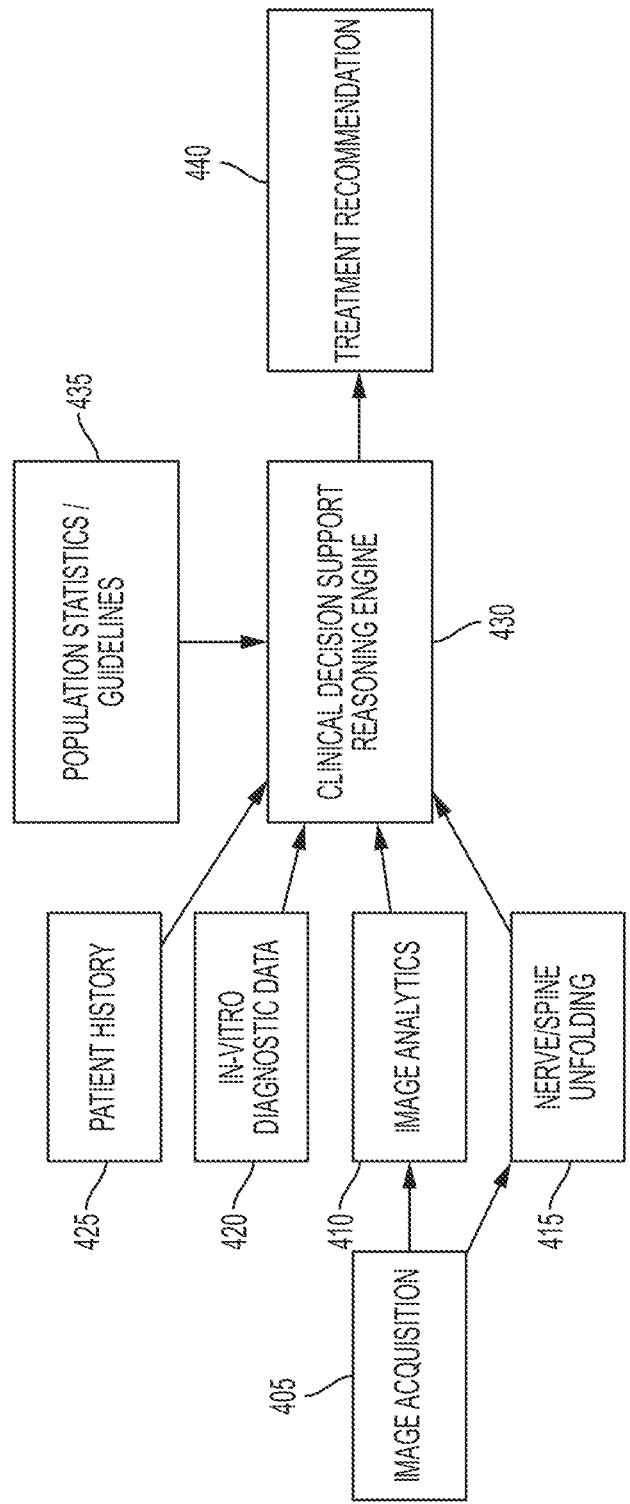
FIG. 4 illustrates a complete system to assist in the rapid data input for clinical decision support engines, according to some embodiments.

FIG. 4 illustrates a complete system to assist in the rapid data input for clinical decision support engines, according to some embodiments of the present invention. An Image Acquisition 405 is automated following a scout scan to determine the orientation of all subsequent scans. Patient History 425 (e.g., clinical, genetic, and demographic data) and In-vitro Diagnostic Data 420 are also used to determine, for example, any additional imaging necessary such a STIR sequence. Once the images are acquired, Image Analytics 410 with deep learning can be used to locate and quantify a variety of elements in the image such as the discs, spine, and bone marrow to assist in automatically filling out quantitative details such as the degree of stenosis. For example, in some embodiments, the Image Analytics 410 uses a deep learning network comprised of 3 convolutional layers and 3 fully connected layers is trained volumetric regions containing labeled normal and degenerative discs. Landmark detection is applied to the given volume to identified disc volumes. Then, the network is applied on each disc and the results are recorded and sent to a CDS Reasoning Engine 430 (or some other form of automated reporting). Additionally, Nerve and Spine Unfolding 415 is used to allow the physician to rapidly examine the entire image set and document any findings into the CDS Reasoning Engine 430. The techniques for Nerve and Spine Unfolding 415 are described above with reference to FIGS. 1-3D The CDS Reasoning Engine 430 combines the image information with Population Statistics/Guidelines 435 to make one or more Treatment Recommendations 440. As is generally known in the art, a CDS system assists clinicians to analyze and diagnosis patient data at the point of care. In some embodiments, the CDS Reasoning Engine 430 comprises a knowledge base if-then rules that allow inferences to be made based on the various data inputs 410, 415, 420, and 425. In other embodiments, the CDS Reasoning Engine 430 uses machine learning to find patterns in clinical data. Examples of machine learning models that may be used by the CDS Reasoning Engine 430 include support vector machines and artificial neural networks. Although the machine learning models may provide a diagnosis in an automated manner, a clinician may interface with the CDS Reasoning Engine 430 following modeling processing to verify or correct predicted treatment recommendations. Aside for decision support, the various data inputs 410, 415, 420, and 425 may also be used by the CDS to support clinical coding and documentation. For example, based on the Image Analytics 410 input, a degenerative disc can be identified, coded, and documented automatically for reference to an insurance agency.

Figure 5:
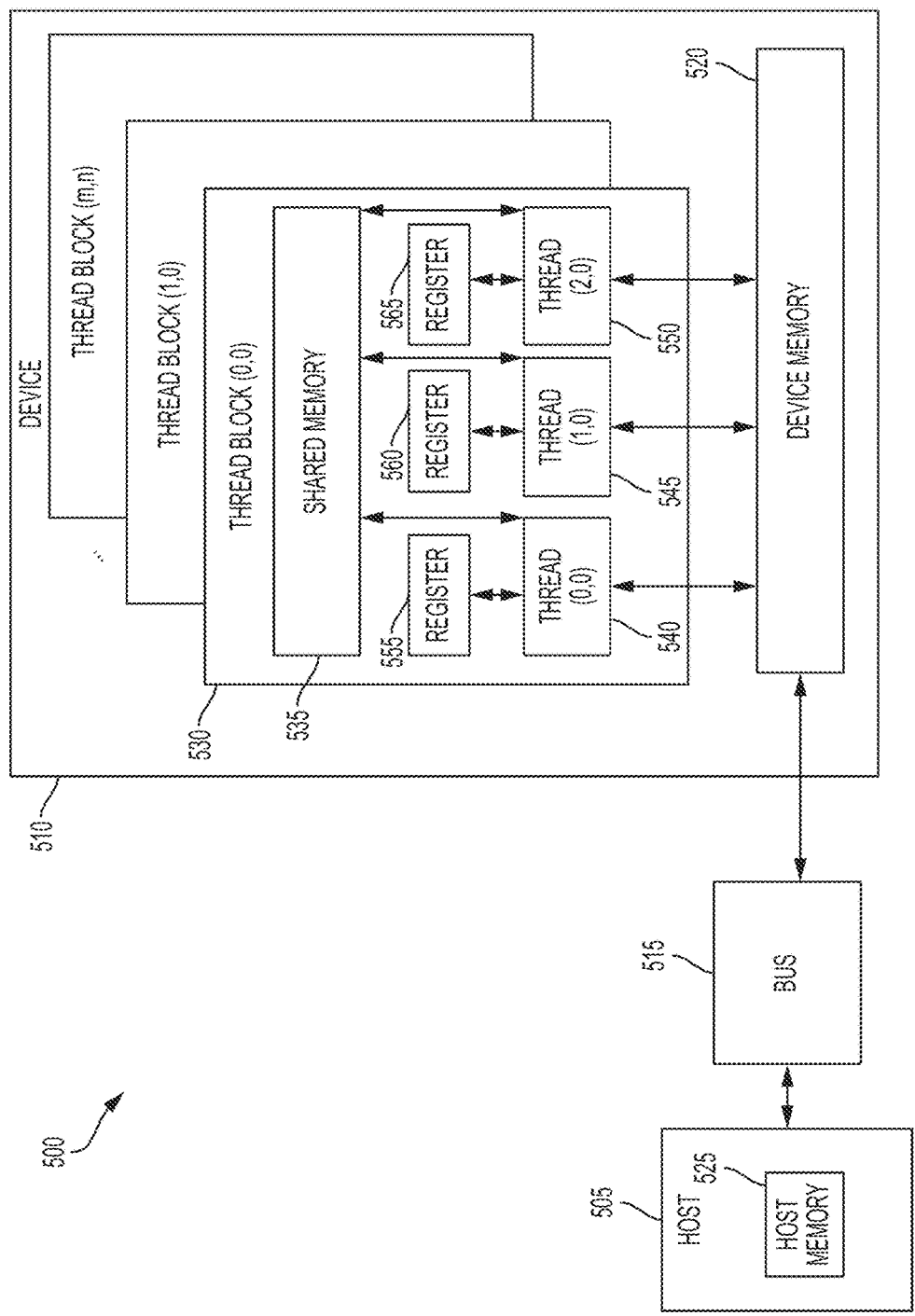
FIG. 5 provides an example of a parallel processing memory architecture that may be utilized in some embodiments.

FIG. 5 provides an example of a parallel processing memory architecture 500 that may be utilized in some embodiments of the present invention. For example, this architecture 500 may be used for bone or nerve unfolding computations, or for implementation of the deep learning network described above with reference to FIG. 4. This architecture 500 may be used in embodiments of the present invention where NVIDIA™ CUDA (or a similar parallel computing platform) is used. The architecture includes a host computing unit ("host") 505 and a GPU device ("device") 510 connected via a bus 515 (e.g., a PCIe bus). The host 505 includes the central processing unit, or "CPU" (not shown in FIG. 5) and host memory 525 accessible to the CPU. The device 510 includes the graphics processing unit (GPU) and its associated memory 520, referred to herein as device memory. The device memory 520 may include various types of memory, each optimized for different memory usages. For example, in some embodiments, the device memory includes global memory, constant memory, and texture memory.

Parallel portions of a deep learning application may be executed on the architecture 500 as "device kernels" or simply "kernels." A kernel comprises parameterized code configured to perform a particular function. The parallel computing platform is configured to execute these kernels in an optimal manner across the architecture 500 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by grid of thread blocks (described in greater detail below). Using concurrent kernel execution, streams, and synchronization with lightweight events, the architecture 500 of FIG. 5 (or similar architectures) may be used to parallelize training of a deep neural network. For example, in some embodiments, a separate kernel is dedicated to each spinal nerve during the unfolding process.

The device 510 includes one or more thread blocks 530 which represent the computation unit of the device 510. The term thread block refers to a group of threads that can cooperate via shared memory and synchronize their execution to coordinate memory accesses. For example, in FIG. 5, threads 540, 545 and 550 operate in thread block 530 and access shared memory 535. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 5, the thread blocks 530 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints. In some embodiments, the individual thread blocks can be selected and configured to optimize training of the deep learning network. For example, in one embodiment, each thread block is assigned a subset of training data with overlapping values. In other embodiments, thread blocks can be dedicated to different vertebral sections included in the spine.

Continuing with reference to FIG. 5, registers 555, 560, and 565 represent the fast memory available to thread block 530. Each register is only accessible by a single thread. Thus, for example, register 555 may only be accessed by thread 540. Conversely, shared memory is allocated per thread block, so all threads in the block have access to the same shared memory. Thus, shared memory 535 is designed to be accessed, in parallel, by each thread 540, 545, and 550 in thread block 530. Threads can access data in shared memory 535 loaded from device memory 520 by other threads within the same thread block (e.g., thread block 530). The device memory 520 is accessed by all blocks of the grid and may be implemented using, for example, Dynamic Random-Access Memory (DRAM).

Each thread can have one or more levels of memory access. For example, in the architecture 500 of FIG. 5, each thread may have three levels of memory access. First, each thread 540, 545, 550, can read and write to its corresponding registers 555, 560, and 565. Registers provide the fastest memory access to threads because there are no synchronization issues and the register is generally located close to a multiprocessor executing the thread. Second, each thread 540, 545, 550 in thread block 530, may read and write data to the shared memory 535 corresponding to that block 530. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 510 to read and/or write to the device memory. Device memory requires the longest time to access because access must be synchronized across the thread blocks operating on the device. Thus, in some embodiments, the processing of each spinal nerve or bone is coded such that it primarily utilizes registers and shared memory and only utilizes device memory as necessary to move data in and out of a thread block.

The embodiments of the present disclosure may be implemented with any combination of hardware and software. For example, aside from parallel processing architecture presented in FIG. 5, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

The invention claimed is:

1. A computer-implemented method for generating inputs for clinical decision support engine based on unfolded spinal image data, the method comprising:
   receiving a 3D image volume depicting a spinal cord, a plurality of vertebra, and a plurality of spinal nerves;
   unfolding the plurality of spinal nerves depicted in the 3D image volume to yield a plurality of unfolded spinal nerves;
   generating a plurality of unfolded spinal nerve images depicting the plurality of unfolded spinal nerves;
   unfolding the plurality of vertebra depicted in the 3D image volume to yield a plurality of unfolded vertebra;
   generating a plurality of unfolded vertebra images depicting the plurality of unfolded vertebra;

determining one or more degenerative spinal elements based on the plurality of unfolded spinal nerve images and the plurality of unfolded vertebra images.

2. The method of claim 1, wherein the one or more degenerative spinal elements are determined based on input received from a clinician in response to presentation of the plurality of unfolded spinal nerve images and the plurality of unfolded vertebra images on a display.

3. The method of claim 1, wherein the one or more degenerative spinal elements are determined automatically by a machine learning network using the plurality of spinal nerve images and the plurality of unfolded vertebra images as input.

4. The method of claim 1, further comprising:
documenting the one or more degenerative spinal elements in a clinical decision support reasoning engine.

5. The method of claim 1, wherein the plurality of spinal nerves depicted in the 3D image volume is unfolded by:
defining a surface within the 3D volume comprising the spinal nerves, wherein the surface is curved such that it passes through the spinal cord while encompassing the spinal nerves; and
identifying voxels on the surface included in the 3D volume.

6. The method of claim 1, wherein the plurality of spinal nerves depicted in the 3D image volume is unfolded by:
segmenting the plurality of spinal nerves depicted in the 3D image volume to yield a plurality of segmented spinal nerves;
for each of the plurality of segmented spinal nerves, identifying a centerline of the segmented spinal nerve; and
unfolding each of the plurality of segmented spinal nerves based on its centerline.

7. The method of claim 6, wherein each unfolded spinal nerve image is generated by selecting voxels from the 3D image volume on each side of the corresponding centerline.

* * * * *